US007686929B2

(12) United States Patent
Toumazou et al.

(10) Patent No.: US 7,686,929 B2
(45) Date of Patent: Mar. 30, 2010

(54) SENSING APPARATUS AND METHOD

(75) Inventors: Christofer Toumazou, Oxford (GB); Sunil Purushothaman, London (GB)

(73) Assignee: DNA Electronics Limited, London (GB)

( * ) Notice: Subject to any disclaimer, the term of this patent is extended or adjusted under 35 U.S.C. 154(b) by 1283 days.

(21) Appl. No.: 10/471,197

(22) PCT Filed: Mar. 11, 2002

(86) PCT No.: PCT/GB02/00965

§ 371 (c)(1), (2), (4) Date: Mar. 2, 2004

(87) PCT Pub. No.: WO03/073088

PCT Pub. Date: Sep. 4, 2003

(65) Prior Publication Data

US 2004/0134798 A1 Jul. 15, 2004

(30) Foreign Application Priority Data

Mar. 9, 2001 (GB) ................................. 0105831.2

(51) Int. Cl.
*G01N 27/327* (2006.01)
*G01N 27/333* (2006.01)
*G01N 27/414* (2006.01)

(52) U.S. Cl. .................. 204/403.01; 204/403.1; 204/416; 257/253

(58) Field of Classification Search ............ 257/253; 204/416–420, 403.01–403.15; 205/777.5, 205/778, 792

See application file for complete search history.

(56) References Cited

U.S. PATENT DOCUMENTS

| 4,467,459 | A | * | 8/1984 | Currie | ................. 367/21 |
| 4,555,623 | A | * | 11/1985 | Bridgewater et al. | ..... 250/214 A |
| 4,777,019 | A | | 10/1988 | Dandekar | ............... 422/68 |
| 4,839,000 | A | * | 6/1989 | Eddowes | ............... 205/778 |
| 5,309,085 | A | * | 5/1994 | Sohn | ................. 257/253 |
| 5,466,348 | A | | 11/1995 | Holm-Kennedy | ....... 204/153.1 |
| 5,543,024 | A | | 8/1996 | Hanazato et al. | |
| 5,632,957 | A | | 5/1997 | Heller et al. | ............... 422/68.1 |
| 5,827,482 | A | | 10/1998 | Shich et al. | |

(Continued)

FOREIGN PATENT DOCUMENTS

EP  0 235 024 A2  9/1987

(Continued)

OTHER PUBLICATIONS

Wong et al. "A CMOS-Integrated "ISFET-Operational Amplifier" Chemical Sensor Employing Differential Sensing" (1989) IEEE Transactions on Electronic Devices, vol. 36, No. 3, pp. 479-487.*

(Continued)

*Primary Examiner*—Alex Noguerola
(74) *Attorney, Agent, or Firm*—Nixon & Vanderhye P.C.

(57) ABSTRACT

A sensing apparatus comprising an ion sensitive field effect transistor arranged to generate an electrical output signal in response to localized fluctuations of ionic charge at or adjacent the surface of the transistor, and means for detecting the electrical output signal from the ion sensitive field effect transistor, the localized fluctuations of ionic charge indicating events occurring during a chemical reaction.

15 Claims, 2 Drawing Sheets

Architecture of ISFET/EnFET coupling

U.S. PATENT DOCUMENTS

| | | | |
|---|---|---|---|
| 6,015,714 A | 1/2000 | Baldarelli et al. | 436/2 |
| 6,060,327 A | 5/2000 | Keen | 436/518 |
| 6,413,792 B1 | 7/2002 | Sauer et al. | 438/49 |
| 6,482,639 B2* | 11/2002 | Snow et al. | 435/287.2 |
| 6,710,263 B2* | 3/2004 | Kobayashi et al. | 174/260 |
| 6,953,958 B2 | 10/2005 | Baxter et al. | 257/253 |
| 7,235,389 B2* | 6/2007 | Lim et al. | 435/174 |
| 2003/0186262 A1 | 10/2003 | Cailloux | 435/6 |
| 2004/0238379 A1* | 12/2004 | Lindsay et al. | 205/792 |
| 2004/0262636 A1 | 12/2004 | Yang et al. | 257/200 |
| 2005/0032075 A1 | 2/2005 | Yaku et al. | 435/6 |
| 2005/0062093 A1 | 3/2005 | Sawada et al. | 257/316 |

FOREIGN PATENT DOCUMENTS

| | | |
|---|---|---|
| JP | 01 102352 A | 4/1989 |
| JP | 02 309241 A | 12/1990 |
| WO | WO 90/13666 | 11/1990 |

OTHER PUBLICATIONS

F. Sterky, J. Lundeberg, "Sequence of genes and genomes," Journal of Biotechnology, vol. 76, pp. 1-31 (2000).

Yuri A. Shakhov, Pal Nyren, "A Sensitive and Rapid Method for Determination of Pyophosphate Activity," Acta Chemica Scandinavica B 36, pp. 689-694 (1982).

R. Buck, "Electrochemistry of Ion-Selective Electrodes," Sensors and Actuators, (1), pp. 197-260 (1981).

P. Woias, L. Meixner, D. Amandi, et al., "Modelling the short-time response of ISFET sensors," Sensors and Actuators B, 24-25, pp. 211-217 (1995).

Taor, S. and Richardson, C.C., "DNA Sequence analysis with a modified bacteriophage T7 DNA polymerase. Effect of pyrophosphorolysis and metal ions," Journal of Biological Chemistry, pp. 8322-8328(1990).

L. Victorova, et al., "New substrates of DNA polymerases," Federal of European Biochemical Societies Letters, 453, pp. 6-10(1999).

Hanzato et al., "Integrated Multi-Biosensors Based on an Ion-sensitive Field-Effect Transistor Using Photolithographic Techniques," IEEE Transactions of Electron Devices, vol. 36, pp. 1303-1310 (1989).

Matsuo, M. Esashi, "Methods of ISFET fabrication," Sensors and Actuators, 1, pp. 77-96 (1981).

N.F. Starodub, W. Torbicz, et al., "Optimisation methods of enzyme integration with transducers for analysis of irreversible inhibitors," Sensors and Actuators B, 58, pp. 420-426 (1999).

Hon-Sumn Wong, Marvin White, "A Self-Contained CMOS Integrated pH sensor," Electron Devices Meeting (1988).

Patent Abstracts of Japan vol. 015, No. 095 (P-1176), Mar. 7, 1991 and JP 02 309241 A (Matsushita Electric Ind Co Ltd), Dec. 25, 1999 abstract.

Patent Abstracts of Japan vol. 013, No. 342 (P-908), Aug. 2, 1989 and JP 01 102352 A (Toshiba Corp), Apr. 20, 1989 abstract.

PCT Notification of Transmittal of the International Search Report or The Declaration for PCT Counterpart Application No. PCT/GB02/00965 Containing International Search Report (Aug. 4, 2003).

Luke Alphey, "DNA Sequencing: From Experimental Method to Bioinformatics," Bios Scientific Publishers Ltd., Oxford, United Kingdom, pp. i-xiv and 1-25 (1997).

Christopher K. Mathews, K.E. van Holde, and Kevin G. Ahern, "Biochemistry, $3^{rd}$ Edition," Addison Wesley Longman, Inc. Benjamin/Cummings, pp. i-xxviv, 57-125, and 980-1026 (2000).

Sakurai and Husimi, "Real-Time Monitoring of DNA Polymerase Reactions by a Micro ISFET pH Sensor," Anal. Chem, 64, pp. 1996-1997 (1992).

\* cited by examiner pH changes during pyrophosphate hydrolysis
(buffered environment)

Enzyme linked Ion Sensitive Field Effect Transistor

Architecture of ISFET/EnFET coupling

Sequencing output (expected) in one cycle (localization of thymine)

SENSING APPARATUS AND METHOD

CROSS-REFERENCE TO RELATED APPLICATIONS

The present application is a National Phase Application of International Application No. PCT/GB02/00965, filed Mar. 11, 2002, which claims priority from Great Britain Patent Application No. 0105831.2, filed Mar. 9, 2001. The present application claims priority from both applications.

FIELD

The present invention relates to a sensing apparatus and method, and particularly though not exclusively to a sensing apparatus and method suitable for DNA sequencing.

BACKGROUND

DNA sequencing methods have remained largely unchanged in the last 20 years [1]. The Sanger method is a well known method of DNA sequencing, and comprises DNA synthesis, with termination of DNA replication at points of di-doxynucleotide insertion. The DNA synthesis is followed by electrophoresis of the synthesised DNA to separate DNA molecules according to their mass to charge ratios, thereby allowing determination of the DNA sequence.

A disadvantage of the Sanger method is that electrophoresis is complex, costly and hazardous.

SUMMARY OF THE INVENTION

It is an object of the present invention to provide a sensing apparatus and method which overcomes or mitigates at least one of the above disadvantages.

According to a first aspect of the invention there is provided a sensing method comprising detecting an electrical signal output from an ion sensitive field effect transistor, and monitoring the detected electrical signal to discriminate localised fluctuations of ionic charge, the localised fluctuations of ionic charge occurring at or adjacent the surface of the field effect transistor indicating events occurring during a chemical reaction.

The inventors have realised that localised fluctuations of ionic charge which occur at the surface of a field effect transistor may be measured. Although ion sensitive field effect transistors are already known, they have previously been used to monitor slow changes of for example absolute values of pH in a reaction mixture as a whole. They have not been used to monitor localised fluctuations of ionic charge. In known arrangement of ion sensitive field effect transistor arrangement, a measurement of the absolute value of the pH of the reaction mixture is made every 30 seconds. Typically, many millions of chemical reactions will occur between measurements, and this is seen as a change of the absolute value of the pH. The invention allows individual events of a chemical reaction to be monitored. Each event will typically comprise several thousand molecules all undergoing the same reaction at the same time.

Preferably, the chemical reaction is DNA synthesis, and the fluctuations of ionic charge indicate the insertion of di-deoxynucleotide triphosphates (ddNTP) and deoxynucleotide triphosphates (dNTP).

A limitation of existing ion sensitive field effect transistor arrangements is that they attempt to measure absolute values of pH, and consequently suffer from drift and hysteresis. The invention monitors fluctuations of ionic charge rather than absolute values, and thus avoids this problem.

Preferably, the time at which the fluctuations occur and the magnitude of the fluctuations is monitored to allow sequencing of DNA or mRNA.

According to a second aspect of the invention there is provided a sensing apparatus comprising an ion sensitive field effect transistor arranged to generate an electrical output signal in response to localised fluctuations of ionic charge at or adjacent the surface of the transistor, means for detecting an electrical output signal from the ion sensitive field effect transistor, and means for monitoring the detected electrical signal to discriminate localised fluctuations of ionic charge, the localised fluctuations of ionic charge indicating events occurring during a chemical reaction.

Preferably, the chemical reaction is DNA synthesis, and the localised fluctuations of ionic charge indicate the insertion of di-deoxynucleotide triphosphates (ddNTP) and deoxynucleotide triphosphates (dNTP).

Preferably, the monitoring means is arranged to monitor the time at which the localised fluctuations occur and the magnitude of the localised fluctuations, to allow sequencing of DNA or mRNA.

BRIEF DESCRIPTION OF THE DRAWINGS

A specific embodiment of the invention will now be described by way of example only with reference to the accompanying figures, in which.

DETAILED DESCRIPTION

DNA sequencing using an embodiment of the invention is performed as follows: A quantity of DNA of interest is amplified using either a polymerase chain reaction or cloning, and the region of interest is primed using mRNA. DNA polymerase catalyses DNA synthesis through the incorporation of nucleotide bases in a growing DNA chain. This is accompanied in vivo with the hydrolysis of pyrophosphate, which at physiological pH leads to the liberation of hydrogen ions [2].

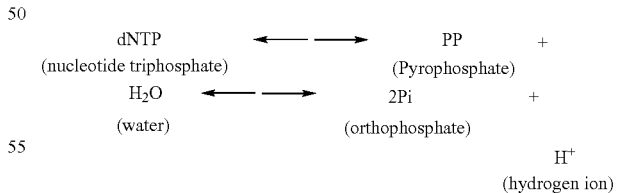

The arrows '←—→' are intended to indicate reversible reactions. The difference between the sizes of the right hand arrows is intended to indicate that it is more energetically favourable to go from Pyrophosphate and water to orthophosphate and a hydrogen ion than vice versa.

Figure 1:
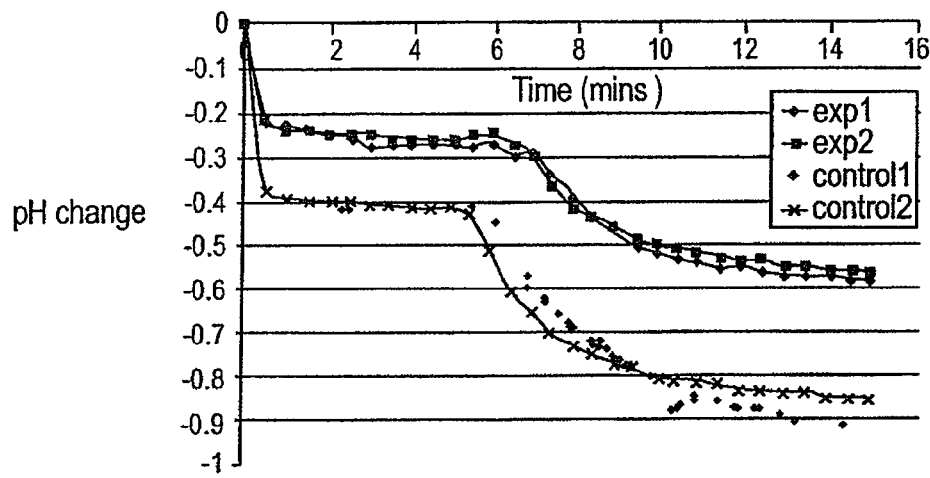
FIG. 1 shows pH changes occurring during pyrophosphate hydrolysis using a buffered reaction medium.

The results shown in FIG. 1 demonstrate the pyrophosphate hydrolysis reaction and its effect on pH. The pH was measured using a glass electrode arrangement, with measurements of the absolute value of pH taken every 30 seconds. The pH can be seen to fall gradually. The embodiment of the invention uses this reaction to monitor nucleotide insertion, by detecting localised fluctuations of pH which occur at or adjacent the surface of an ion sensitive field effect transistor (FET).

The FET is provided with an ion sensitive silicon nitride layer, on top of which a layer of polymerase is provided. Hydrolysis of pyrophosphate by pyrophosphatase which remains bound on the polymerase enzyme [7] is detected by the FET. The hydrolysis is indicative of nucleotide insertion during DNA synthesis. The magnitude of pH change in either direction (i.e. positive or negative) is detected in order to reliably detect nucleotide insertion, as described below. Individual nucleotide insertion will occur approximately every 3 ms at a temperature of 65 C, [6]). The FET is able to detect rapid pH changes and has an immediate response rate measured to be within 1 ms of a pH change [5].

The hydrolysis of pyrophosphate causes either a net production or consumption of hydrogen ions depending on the pH in which the reaction occurs. In the embodiment of the invention the reaction is conducted at pH 6.8. At pH 6.8 hydrogen ions are overall consumed rather than liberated during nucleotide insertion. The embodiment of the invention thus monitors rises in pH as indicators of nucleotide insertion.

Figure 2:
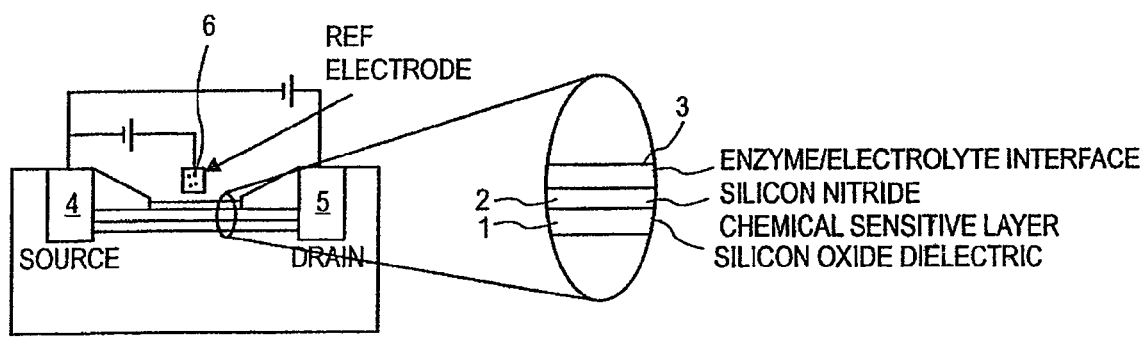
FIG. 2 is a schematic diagram of a field effect transistor which embodies the invention.

A pH sensitive FET which embodies the invention is shown in FIG. 2. The FET is similar to a traditional MOSFET (Metal Oxide Semiconductor Field Effect Transistor). The FET comprises a silicon oxide dielectric layer 1, a silicon nitride chemical sensitive layer 2, and an enzyme/electrolyte interface 3. The layers 1, 2 and interface 3 are located between a source 4 and drain 5 (the conventional configuration of a FET). The FET is provided on a silicon chip, which is encapsulated in epoxy resin to protect it from the reagent mixture. The epoxy resin helps to protect the FET from hydration and charge migration [9]. The FET itself is not covered by epoxy resin, so that it may be immersed in the reagent mixture.

The enzyme/electrolyte interface 3 shown in FIG. 2 allows ion sensitivity of the silicon nitride layer 2 to be used for DNA sequencing. The FET functions by producing an exchange of charged ions between the surface of the chemical sensitive layer 2 and the reacting medium (i.e. the enzyme/electrolyte interface 3):

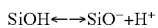

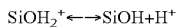

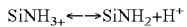

The inclusion of silicon nitride is advantageous because it provides increased and faster sensitivity to changes of pH than would be obtained in the absence of the silicon nitride. In addition the silicon nitride helps to protect the FET from hydration and charge migration.

A non-Nernstian response accounts for the immediate sensitivity of the FET, arising from rapid proton dependant binding and unbinding of charged ions at the insulating gate silicon nitride surface, which results in a reproducible variation in the voltage drop across the silicon nitride layer 2. The variation of the voltage drop across the silicon nitride layer 2 correlates with changes of pH. The voltage drop is monitored using instrumentation circuitry, thereby allowing the detection of individual nucleotide insertions. The measured voltage is referred to as the flatband voltage.

The enzyme/electrolyte interface 3 is deposited on the silicon nitride layer using a known enzyme linkage method [10)]. The method comprises pre-silanising the silicon nitride layer 2 using aminosilane solution, and then activating the surface using glutaraldehyde. A drop of buffer/polymerase enzyme solution is then deposited on the silicon nitride layer 2 and allowed to dry for about half an hour to form the enzyme layer 3.

The embodiment shown in FIG. 2 uses a reference electrode 6 to provide a measurement of pH changes. The reference electrode is relatively large and difficult to fabricate. An alternative embodiment of the invention does not use a reference electrode, but instead uses a second FET which has the same construction as the first FET, but is provided with a non-enzyme linked layer instead of the enzyme layer 3. This configuration is advantageous because it provides a differential measurement which gives an improved signal to noise ratio.

Figure 3:
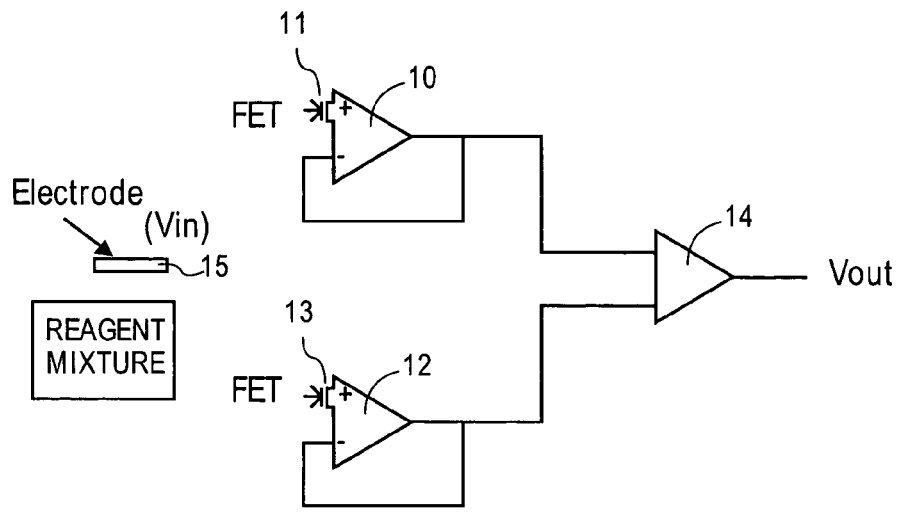
FIG. 3 is a schematic diagram of a pair of field effect transistors which embody the invention.

The alternative embodiment of the invention is illustrated in FIG. 3. The configuration of this embodiment is based upon a known construction [11] which has previously been used to monitor gradual slow drift of pH. The embodiment comprises a first operational amplifier 10 to which the source of the first FET 11 is connected (the first FET has the enzyme linked layer), and a second operational amplifier 12 to which the source of the second FET 13 is connected (the second FET has the non-enzyme linked layer). The drains of the first and second FETs are connected to a fixed current source (not shown). Outputs from the first and second operational amplifiers are passed to a differential amplifier 14, which amplifies the difference between the outputs to generate an output signal $V_{out}$. Negative feedback from the differential amplifier 14 passes to a noble electrode 15 which is located in the reagent mixture. The operational amplifier 14 generates an output voltage which keeps the voltage applied to the FETs 11, 13 the same despite changes of hydrogen concentration.

The embodiment shown in FIG. 3 is advantageous because it allows rationalisation of fabrication of the FET's 11, 13 and the operational amplifiers 10, 12, 15.

The FET's 11, 13 may be arranged to form the first stage of the operational amplifiers 10, 12. This is done for each operational amplifier by replacing a conventional FET of a long tail pair located at the input of the operational amplifier, with the first or second FET 11, 13. This is advantageous because it allows the first and second FETs to form part of the amplification circuitry.

Figure 4:
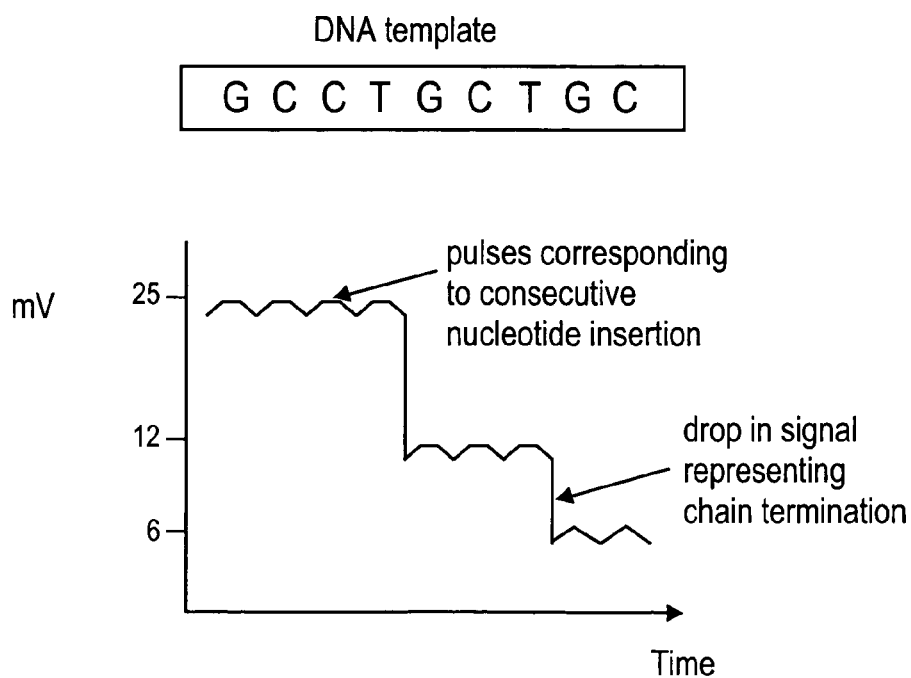
FIG. 4 is a schematic representation of results obtained using the pair of field effect transistors.

A schematic example of a flatband voltage detected using the embodiment shown in FIG. 3 is illustrated in FIG. 4. The example is for an NMOS FET with the reaction operating in the ion consumption mode, as described above (the figure would be inverted for a PMOS FET or if the reaction was operating in the ion liberation mode). The flatband voltage consists of pulses representing pH changes associated with nucleotide insertion and drops corresponding to ddNTP insertion and chain termination. The number of local pulses prior to a larger drop determines the number of bases present before termination at a known base; the magnitude of the larger drop is dependant on the ratio of ddNTP:dNTP used in the reagent mixture and is important due to the dependence of read length for that drop. Through repetition of the process four times in different reaction chambers containing each of the four ddNTPS seperately, the complete sequence is delineated.

Referring to FIG. 4 in detail, DNA synthesis is performed with termination of DNA synthesis at points of di-doxynucleotide insertion of thymine bases. Each individual nucleotide insertion causes the liberation of a hydrogen ion, and these are detected as pulses of the flatband voltage, as can be seen in FIG. 4. When the DNA chain reaches a thymine base, nucleotide insertion is prevented for some of the DNA chains, and the amount of hydrogen ion consumption drops leading to a drop in signal output. DNA synthesis continues for those DNA chains which were not terminated at the thymine base, and this is seen as pulses of the flatband voltage at the new lower level. The flatband voltage falls again when the DNA chain reaches a second thymine base, and then continues to pulse at the lower level.

The method may be used with or without thermocycling. For example, thermocycling may be used to facilitate optimisation, using taq polymerase as a sequencing enzyme [12]. The pH of the reagent mixture may be adjusted for example. A decrease of the pH will lead to the production of more hydrogen ions, but will also tend to kill off the reaction. Trials have shown pH 6.8 to be a useful value of pH. Magnesium may be added to the reagent mixture to actuate the enzyme. The concentrations of the reagents may be modified.

A typical thermocycling sequence is set out in table 1.

TABLE 1

| Cycle Sequencing | | |
| --- | --- | --- |
| Temperature | Duration | Function |
| 95° C. | 30 sec | Denaturing of DNA template |
| 55° C. | 30 sec | Annealing of primer |
| 72° C. | 60 sec | DNA extension and termination |

Operating within a thermal cycler enables multiple repetition of the sequencing process with minimal manipulation. This allows signal to noise boosting and easier delineation of difficult to read regions such as GC rich regions or areas of single nucleotide repeats.

Recombinant T7 polymerase may be used instead of taq polymerase. Where T7 polymerase is used, this may provide increased speed and improved accuracy of monitoring nucleotide insertion.

The steps used to fabricate the enzyme sensitive FET are set out below in table 2:

TABLE 2

PURIFIED SILICON SUBSTRATE
ADDITION OF DOPANT: PRODUCTION OF p-TYPE SUBSTRATE
SURFACE OXIDATION: $SiO_2$ LAYER GENERATION
SOURCE/DRAIN DEFINITION AND IMPLANTATION
SILICON NITRITE DEPOSITION USING LPCVD*
CONTACT FORMATION
PASSIVATION
PURIFIED SILICON SUBSTRATE
ADDITION OF DOPANT: PRODUCTION OF p-TYPE SUBSTRATE
SURFACE OXIDATION: $SiO_2$ LAYER GENERATION
SOURCE/DRAIN DEFINITION AND IMPLANTATION
SILICON NITRITE DEPOSITION USING LPCVD*
CONTACT FORMATION
PASSIVATION

The FETs, and in particular those shown in FIG. 3, and the amplification stages may be replaced or combined with PMOS transistors operating in the weak inversion region. This is advantageous because it allows the exponential gain produced by the PMOS transistors to be used. Where this is done an otherwise decaying signal may be made to behave conversely and rise.

The length of DNA that can be sequenced will normally be limited by the signal to noise at distal bases as the signal decays with ddNTP insertion. Using PMOS FETs should allow extension of the read length, but may involve a possible compromise over the location of more proximal bases. Installation of two separate FET circuits, of the type shown in FIG. 3, one NMOS pair of FETs and one PMOS pair of FETs should provide the optimum read length. Biasing in weak inversion is possible, since the measurement to be made is of changes to output, rather than absolute values, and absolute linearity in signal amplification for signal analysis is not required.

Measurements may be repeated to provide improved signal to noise ratios.

REFERENCES

1) F. Sterky, J. Lundeberg, "Sequence of genes and genomes," *Journal of Biotechnology* vol. 76, pp. 1-31, 2000.

2) Mathews, Holde, Ahern, *Biochemistry*, $2^{nd\ Edn}$

3) Yuri A. Shakhov, Pal Nyren, 'A Sensitive and Rapid Method for Determination of Pyrophosphate Activity' Acta Chemica Scandinavica B 36 (1982) pp 689-694

4) R. Buck, "Electrochemistry of Ion-Selective Electrodes," Sensors and Actuators, (1), pp. 197-260, 1981

5) P. Woias, L. Meixner, D. Amandi, et. al, "Modelling the short-time response of ISFET sensors," *Sensors and Actuators B*. 24-25 pp. 211-217, 1995

6) Taor, S. and Richardson, C. C, "DNA Sequence analysis with a modified bacteriophage T7 DNA polymerase. Effect of pyrophosphorolysis and metal ions" *Journal of Biological Chemistry*, pp8322 8328, 1990

7) L. Victorova, et. al, "New substrates of DNA polymerases," *Federation of European Biochemical Societies* Letters, 453 pp. 6-10, 1999

8) Hanazato et al., "Integrated Multi-Biosensors Based on an Ion-sensitive Field-Effect Transistor Using Photolithographic Techniques," *IEEE Transactions of Electron Devices* vol. 36 pp. 1303-1310, 1989.

9) Matsuo, M. Esashi, "Methods of ISFET fabrication," *Sensors and Actuators,* 1 pp. 77-96, 1981

10) N. F. Starodub, W. Torbicz. et. al, "Optimisation methods of enzyme integration with transducers for analysis of irreversible inhibitors," Sensors and Actuators B, 58 pp. 420-426, 1999

11) Hon-Sum Wong, Marvin White, "A Self-Contained CMOS Integrated pH Sensor," *Electron Devices Meeting*, 12) Alphey Luke, "*DNA sequencing: from experimental methods to bioinformatics*"

What is claimed is:

1. A sensing apparatus comprising two ion sensitive field effect transistors, which are arranged to generate an electrical output signal in response to a chemical reaction to which the transistors are exposed and means for discriminating discrete fluctuation in the electrical output signal, the discrete fluctuations indicating reaction intermediaries occurring during the chemical reaction, a first of the transistors being provided with an enzyme linked layer and a second of the transistors being provided with a non-enzyme linked layer; and said apparatus further comprising means for determining the difference between the electrical signals generated by said first and second transistors to provide said electrical output signal.

2. The sensing apparatus according to claim 1, wherein said first and second transistors are connected to first and second operational amplifiers, and the outputs of the operational amplifiers are passed to a differential amplifier which provides the electrical output signal.

3. The sensing apparatus according to claim 2, wherein the electrical output signal is passed to an electrode located in the reagent mixture, to maintain voltages applied to said first and second transistors at a constant level.

4. The sensing apparatus according to claim 2 or claim 3, wherein said and second transistors are arranged to form part of the first and second operational amplifiers respectively.

5. The sensing apparatus according to claim 1, wherein said two ion sensitive field effect transistors are both PMOS transistors arranged to operate in the weak inversion region.

6. The sensing apparatus according to claim 1, wherein said two ion sensitive field effect transistors are both NMOS transistors arranged to operate in the weak inversion region.

7. The sensing apparatus according to claim 1, wherein the apparatus is configured to generate an electrical output signal in response to ion consumption or ion liberation.

8. The sensing apparatus according to claim 1, wherein said first and second ion sensitive field effect transistors are provided with a layer of silicon nitride.

9. The sensing apparatus according to claim 1, wherein the enzyme of said enzyme-linked layer is provided over a layer of silicon nitride.

10. The sensing apparatus according to claim 1, wherein said first and second ion sensitive field effect transistors are provided as part of an integrated circuit which is substantially covered by epoxy resin and the field effect transistors are not covered by the epoxy resin.

11. The sensing apparatus according to claim 1, wherein the enzyme-linked layer comprises polymerase.

12. The sensing apparatus according to claim 11, wherein said chemical reaction to be detected is nucleotide chain extension, the enzyme of said enzyme-linked layer comprises polymerase and the insertion of a di-deoxynucleotide triphosphate (ddNTP) at the end of the chain is detected.

13. The sensing apparatus according to claim 11, wherein the chemical reaction to be detected is DNA synthesis, the enzyme of said enzyme-linked layer comprises a polymerase and the discrete fluctuations in electrical signal indicate the insertion of one or more deoxynucleotide triphosphates (dNTPs) or termination of DNA synthesis by insertion of a di-deoxynucleotide triphosphate (ddNTP).

14. The sensing apparatus according to claim 13 which further comprises monitoring means arranged to monitor the time at which the discrete fluctuations occur and the magnitude of the discrete fluctuations to allow sequencing of DNA or mRNA.

15. The sensing apparatus according to claim 1 which is configured to generate the electrical output signal in response to a pyrophosphate hydrolysis reaction.

* * * * *